United States Patent
Barbot et al.

(10) Patent No.: US 9,186,088 B2
(45) Date of Patent: Nov. 17, 2015

(54) ACTIVE CATHETER RECONSTRUCTION FOR INTERVENTIONAL MAGNETIC RESONANCE IMAGING

(75) Inventors: Julien Christian Barbot, Princeton, NJ (US); Klaus J. Kirchberg, Plainsboro, NJ (US)

(73) Assignee: Siemens Aktiengesellschaft, Munich (DE)

(*) Notice: Subject to any disclaimer, the term of this patent is extended or adjusted under 35 U.S.C. 154(b) by 305 days.

(21) Appl. No.: 13/611,529

(22) Filed: Sep. 12, 2012

(65) Prior Publication Data
US 2013/0083988 A1    Apr. 4, 2013

Related U.S. Application Data

(60) Provisional application No. 61/540,789, filed on Sep. 29, 2011.

(51) Int. Cl.
*G06K 9/00* (2006.01)
*A61B 5/06* (2006.01)
*A61B 19/00* (2006.01)

(52) U.S. Cl.
CPC .............. *A61B 5/064* (2013.01); *A61B 19/50* (2013.01); *A61B 2019/5483* (2013.01)

(58) Field of Classification Search
None
See application file for complete search history.

(56) References Cited

U.S. PATENT DOCUMENTS

| | | | |
|---|---|---|---|
| 2007/0088530 A1* | 4/2007 | Erignac et al. | 703/1 |
| 2008/0129731 A1* | 6/2008 | Spicer et al. | 345/423 |
| 2009/0284550 A1* | 11/2009 | Shimada et al. | 345/619 |
| 2010/0082248 A1* | 4/2010 | Dorum et al. | 701/209 |
| 2010/0312095 A1* | 12/2010 | Jenkins et al. | 600/411 |
| 2011/0046999 A1* | 2/2011 | Nielsen et al. | 705/7.39 |

FOREIGN PATENT DOCUMENTS

| | | |
|---|---|---|
| CN | 101141929 A | 3/2008 |
| CN | 101371784 A | 2/2009 |
| CN | 101371784 B | 7/2012 |
| CN | 101141929 B | 5/2013 |
| WO | 2006056199 A1 | 6/2006 |

OTHER PUBLICATIONS

Chinese Office Action mailed Mar. 12, 2015 corresponding to Chinese Application No. 201210367204.x filed Sep. 28, 2012 (32 pages).

* cited by examiner

*Primary Examiner* — Atiba O Fitzpatrick

(57) ABSTRACT

A method for device visualization includes receiving a set of physical characteristics including a description of spatial relationships of a plurality of markers within a device. Radiographic data of the device within a subject is acquired. An approximate location of each of the plurality of markers is identified within the radiographic data. A trajectory function is constructed for the device within the subject based on the identified approximate locations of each of the markers and the received set of physical characteristics. A section function is constructed for the device based on the set of physical characteristics and a 3D model is generated for the device based on the constructed trajectory function and the section function. A rendering of the 3D model is displayed on a display device.

22 Claims, 7 Drawing Sheets

US 9,186,088 B2

ACTIVE CATHETER RECONSTRUCTION FOR INTERVENTIONAL MAGNETIC RESONANCE IMAGING

CROSS-REFERENCE TO RELATED APPLICATION

The present application is based on provisional application Ser. No. 61/540,789, filed Sep. 29, 2011, the entire contents of which are herein incorporated by reference.

TECHNICAL FIELD

The present disclosure relates to magnetic resonance imaging and, more specifically, to active catheter reconstruction for interventional magnetic resonance imaging.

DISCUSSION OF THE RELATED ART

Cardiac dysrhythmia (arrhythmia) is characterized by abnormal electrical activity in the heart. Cardiac dysrhythmia may cause the heart to beat too fast, too slow, or irregularly and may be a life-threatening condition. Atrial fibrillation is a particularly common form of cardiac dysrhythmia. Here, the upper two chambers of the heart, known as atria, beat at irregular intervals. This irregular beating may be caused by abnormal electrical impulses that may be produced by diseased or damaged cardiac tissue. Chronic atrial fibrillation, and other forms of cardiac dysrhythmia may place patients at greater risk for certain conditions such as stroke.

Treatments such as catheter ablation may be used to treat cardiac dysrhythmia such as atrial fibrillation. In catheter ablation, catheters are inserted into a patient's blood vessels and then advanced towards the heart. When contact is made with cardiac tissue that is responsible for generating abnormal electrical impulses, the catheter is used to destroy the responsible tissue so that normal electrical impulse may be restored. Ablation of the responsible tissue is generally performed using heat. Pulmonary vein ablation, also called pulmonary vein antrum isolation or PVAI, is a common treatment for atrial fibrillation.

Proper visualization is an important factor in successful intervention such as in performing PVAI. In visualization, the location of the catheter, guide wire, or other instrument may be visually represented to the medical practitioner performing the intervention, for example, by superimposing the location of the catheter over a medical image so that the medical practitioner can accurately guide the catheter to its destination while minimizing risk of complications such as perforation.

SUMMARY

A method for device visualization includes receiving a set of physical characteristics including a description of spatial relationships of a plurality of markers within a device. Radiographic data of the device within a subject is acquired. An approximate location of each of the plurality of markers is identified within the radiographic data. A trajectory function is constructed for the device within the subject based on the identified approximate locations of each of the markers and the received set of physical characteristics. A section function is constructed for the device based on the set of physical characteristics. A 3D model is generated for the device based on the constructed trajectory function and the section function. A rendering of the 3D model is displayed on a display device.

The device may be a catheter and the plurality of markers may include one or more micro-coils. The set of physical characteristics may include distances between adjacent micro-coils of the one or more micro-coils and a measure of maximum possible curvature or bending of the catheter. The trajectory function may be a mathematical spline function defined by a knot vector, a vector of control points, and a degree of polynomial for the spline function. The knot vector and the vector of control points may be varied to find a spline function which satisfies one or more constraints of the received set of physical characteristics. The spline function may be a piecewise-polynomial function of a given degree of polynomial. The degree of polynomial for the spline function may be three. A curve energy of the spline function may be minimized. The spline function may be a B-spline function. The spline function may be a non-uniform rational B-spline (NURBS) function.

The radiographic data may be an MR image.

The section function may be of a predetermined shape. The predetermined shape may be a circle. The radius of the circle may be dependent upon a length along the trajectory function.

The 3D model may be a 3D mesh and the 3D mesh may include sweeping the section function along the trajectory function. Constructing the trajectory function may include interpolating a curve of the trajectory function through each of the identified approximate locations of the markers in a particular order. Constructing the trajectory function may include approximating a curve of the trajectory function by permitting the curve to not intersect each identified approximate locations of the markers and by minimizing a sum of errors calculated as a distance between each identified approximate location of the markers and a corresponding point along the curve.

Identifying an approximate location of each of the plurality of markers within the radiographic data may include determining a confidence or probability for the approximate locations.

Prior to generating the 3D model, it may be determined whether the trajectory function is degenerative and where the trajectory function is determined to be degenerative, a warning message is displayed on the display device.

A method for providing visualization for intervention guidance includes acquiring a radiographic study. A set of markers is identified within a device is identified within the acquired radiographic study. A curve is fit to the identified set of markers according to locations of the identified set of markers within the radiographic study and a prior knowledge of physical characteristics of the device. A 3D model for the device is generated by aligning a deformable model of the device over the fitted curve. A rendering of the 3D model is displayed on a display device for intervention guidance. The a prior knowledge of physical characteristics of the device includes distances between markers within the device and a maximum possible degree of curvature or bending of the device.

The curve may be a mathematical spline function defined by a knot vector, a vector of control points, and a degree of polynomial for the spline function and the knot vector and the vector of control points may be varied to find a spline function which satisfies one or more constraints of the a prior knowledge of the physical characteristics of the device.

Generating the 3D model for the device may include sweeping a section curve along the fitted curve.

A computer system includes a processor and a non-transitory, tangible, program storage medium, readable by the computer system, embodying a program of instructions executable by the processor to perform method steps for device visualization. The method includes receiving a set of physical characteristics including a description of spatial relationships of a plurality of markers within a device. A radiographic scan of the device within a subject is acquired. An approximate location of each of the plurality of markers is identified within the radiographic scan. A mathematical spline function is constructed for the device within the subject based on the identified approximate locations of each of the markers and the received set of physical characteristics. A 3D model for the device is generated based on the constructed spline function. A rendering of the 3D model is displayed on a display device.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION OF THE DRAWINGS

Figure 1:
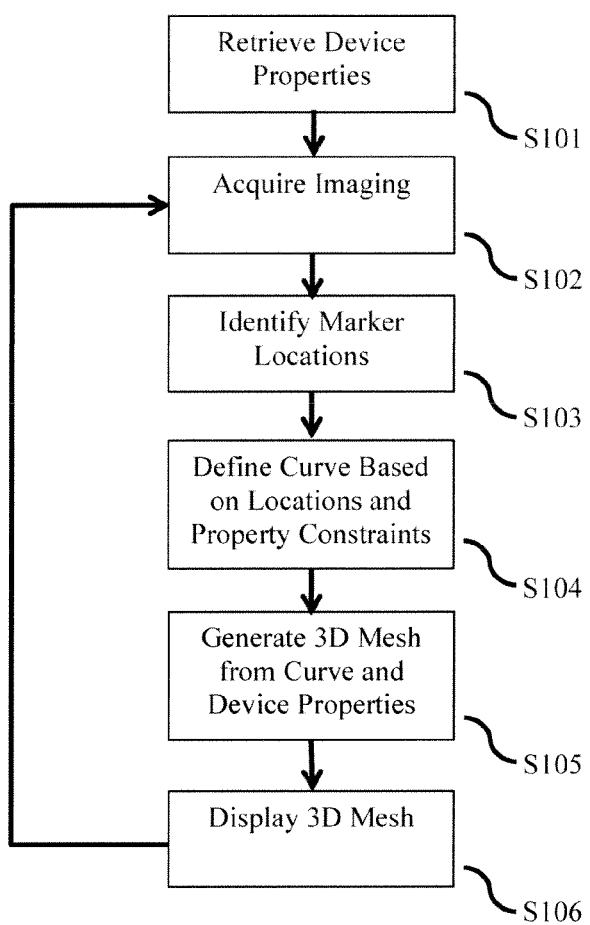
FIG. 1 is a flow chart illustrating method steps for providing intervention visualization in accordance with exemplary embodiments of the present invention.

In describing exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Exemplary embodiments of the present invention provide an approach for precisely localizing a medical device such as a catheter or guidewire during intervention. Rather than relying upon fluoroscopy, which exposes the patient to a continuous dose of potentially harmful ionizing radiation, exemplary embodiments of the present invention employ magnetic resonance (MR) imaging techniques to provide continuous or periodic telemetry for visualization. To enhance the visibility of the medical device, passive or active markers may be embedded therein. While a passive marker is simply an object constructed of a material known to present clearly within the imaging modality being employed, an active marker is one that transmits an identifiable signal when exposed to the imaging modality.

One example of a suitable active marker is a micro-coil, which may be embedded into the medical device at various positions so that identifiable signals may be generated when exposed to the imaging modality.

While exemplary embodiments of the present invention are described herein with reference to active markers and MR imaging, it is to be understood that these techniques may be applied regardless of the type of markers used or the imaging modality used. For example, the marker may be passive markers constructed from a radiopaque material and the imaging modality may be fluoroscopy.

Regardless of the types of markers used, exemplary embodiments of the present invention utilize prior knowledge of the geometry of the medical instrument and the relative position of the markers embedded therein and accordingly, these specifications may be known and retrievable.

During the intervention, location information pertaining to the markers is observed and used to construct a curve, which is constrained by the prior knowledge of the instrument geometry. A three-dimensional (3D) mesh may then be constructed from the curve and the prior knowledge of the geometry of the medical instrument. The constructed 3D mesh may be displayed to the medical practitioner to provide guidance during the intervention.

FIG. 1 is a flow chart illustrating method steps for providing intervention visualization in accordance with exemplary embodiments of the present invention. The physical properties of the medical device may be known a-priori. These physical properties may be stored, for example, as a shape model or as a set of characteristics and then retrieved during or prior to the intervention (Step S101). Medical image data may then be acquired (Step S102). The medical image data may be MR image data acquired from an MR scanner. The medical image data may be continuously or periodically acquired.

From the medical image data, various inputs may be measured (Step S103). These inputs may include the observed location of each marker within the medical device and, where available, a measure of confidence for one or more of the observed locations. The observed location of each marker may include a measured position with one-dimensional (1D) projections along all three spatial directions (x, y, and z). The result may be a set of three-dimensional coordinates for each marker. Where the makers include micro-coils, specialized MR acquisitions may be used to determine these location coordinates.

A curve may then be defined based on the marker location coordinates, the measures of confidence, where available, and geometric constrains derived from the known physical properties of the medical device (Step S104). The curve may represent a model of the physical shape of the medical device as defined by the markers. As the medical device may be flexible and may distort as it navigates through the patient's body, a mathematical function selected to represent the curve may be capable of expressing the distortion in a natural way. Exemplary embodiments of the present invention may utilize a piecewise-polynomial function to represent the curve. For example, a spline function such as a B-spline function may be used. According to some exemplary embodiments of the present invention, the spline function may also be a non-uniform rational B-spline (NURBS) function.

Figure 4:
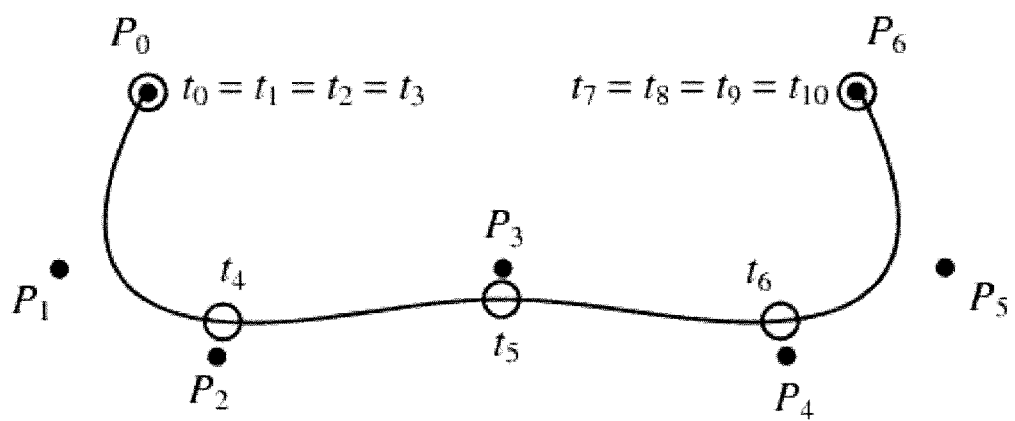
FIG. 4 is an illustration of a B-spline function used to represent the medical device curve in accordance with exemplary embodiments of the present invention.

FIG. 4 is an illustration of a B-spline function used to represent the medical device curve in accordance with exemplary embodiments of the present invention. As may be seen in the figure, a unique B-spline function may be defined by three parameters. These parameters may include a knot vector $t_i$, a vector of control points (de Boor points) $P_i$, and a degree of the polynomial n. Here, i represents the numbered marker locations $i=0 \ldots i_{max}$. The degree of polynomial n may be selected to provide a high degree of freedom while providing smoothness, second order derivative continuity, and while avoiding the introduction of Runge's phenomenon, a quick oscillation of the curve. For these purposes, the degree of polynomial n may be set as 3. However, it is to be understood that other selections may be utilized.

The parameters $t_i$ and $P_i$ may then be varied to find a spline function which satisfies a set of constraints derived from the physical properties of the medical device that are known a-priori, the device properties retrieved in Step S101. The set of physical constraints may be selected based on observations about the medical device's ability to distort in shape while in use.

Figure 3:
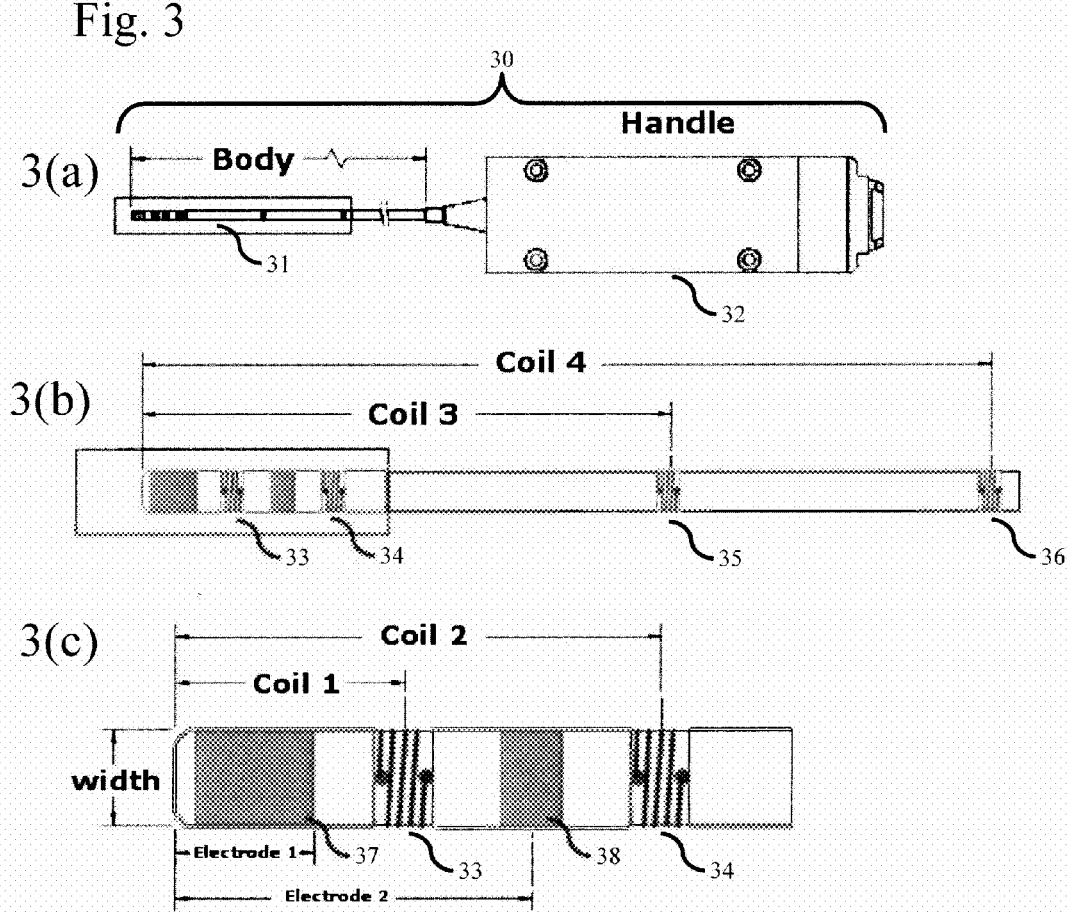
FIG. 3 is a diagram illustrating a medical device and a set of physical properties that may be used in accordance with exemplary embodiments of the present invention.

FIG. 3 is a diagram illustrating a medical device and a set of physical properties that may be used in accordance with exemplary embodiments of the present invention. FIG. 3(a) illustrates a catheter device 30 having a handle section 32 and a body section 31. FIG. 3(b) provides a close-up view of the section boxed in FIG. 3(a) and FIG. 3(c) provides a close-up view of the section of boxed in FIG. 3(b). As can be seen by these figures, the physical properties of the catheter 30 may include a width of the catheter body, a location of a first coil 33 with respect to a fixed point along the catheter (here the body end), a location of a second coil 34, a location of a third coil 35, a location of a fourth coil 36, a location of a first electrode 37, and a location of a second electrode 38. It is to be understood that the medical device is not limited to a catheter and that there is no limit to the number of markers (here coils) and electrodes (or other location of interest) that may be included as the a-priori knowledge of the physical properties.

As shown in the exemplary medical device of FIG. 3, exemplary physical constraints may include: (1) a length of the device body between each pair of neighboring coils, (2) a measure of maximum possible curvature of bending of the device, and (3) a minimization of curve energy. Minimization of curve energy may be used as an expression of the physical constraint that the device will have no cusps or loops.

From the physical constraints, optimal variations may be found for parameters $t_i$ and $P_i$. A best curve function may then be found to fit the B-spline to the parameter points, for example, as illustrated in FIG. 4. If confidence information (either discrete or a distribution function) is available, an approximation algorithm may be used to fit the curve with deference to the confidence. If confidence information is not available exact interpolation through the points may be used to fit the curve. The best curve may be expected to provide a realistic shape and a curve may be rejected where the shape is determined to be unrealistic.

A 3D rendering may then be generated from the fitted curve (Step S105). The 3D rendering may serve as a 3D representation of the geometry of the medical instrument. Various approaches may be used to create the 3D rendering. For example, the 3D rendering may be a 3D mesh generated by sweeping a section function along the trajectory of the curve function. If the curve is not plausible, then the 3D rendering might not be generated and a warning may be displayed.

Thereafter, the 3D rendering may be displayed on a display device (Step S106) using a graphics rendering device such as a graphics processing unit (GPU) that is either integrated onto a central processing unit (CPU) or provided as a discrete graphics processing device.

Figure 2:
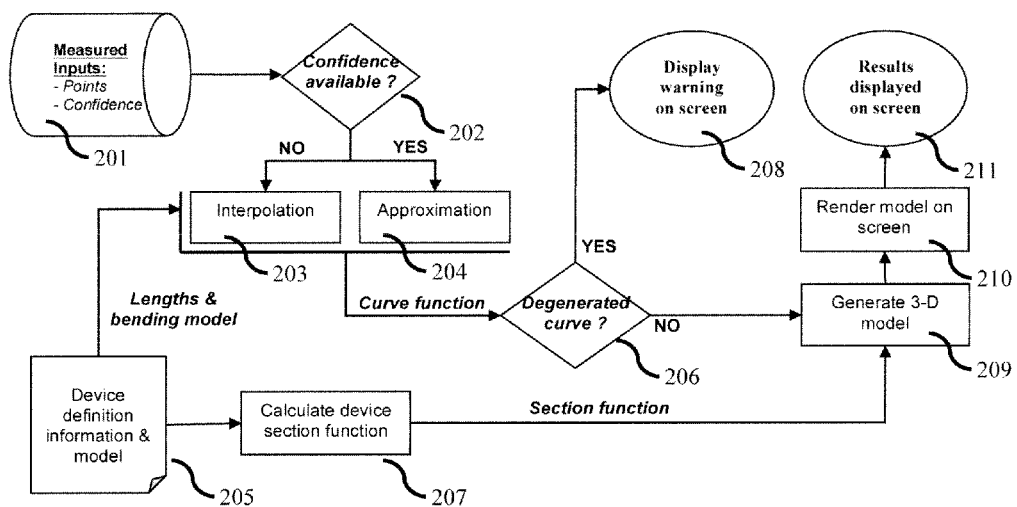
FIG. 2 is a flow chart illustrating an approach for providing medical device reconstruction in accordance with exemplary embodiments of the present invention.

FIG. 2 is a flow chart illustrating an approach for providing medical device reconstruction in accordance with exemplary embodiments of the present invention. Here, method steps are illustrated in conjunction with data inputs and outputs. First, measured inputs 201 may be provided. As discussed above the measured inputs may include locations of markers such as micro-coils identified within the imaging data and, where available, confidence intervals. Where no confidence or probability data is available for the measured point locations or where available confidence/probability data indicates a high degree of accuracy (e.g., as defined by a predetermined threshold value) (No, 202) then an interpolation approach 203 may be used to provide the curve function. Alternatively, where confidence data is available and the confidence data does not indicate a high degree of accuracy (Yes, 202) then an approximation approach 204 may be used to provide the curve function. As an alternative, the degree of accuracy might not be considered and the interpolation approach 203 may be used where no accuracy/probability data is available and the approximation approach 204 may be used where such data is available.

According to the interpolation approach 203, the interpolating curve passes though all given data points in their given order, which may be the order in which the markers are known to be aligned within the device.

The approximation approach 204 may be use to overcome problems associated with noisy measurements in signal acquisition and/or related to signal interference caused by neighboring anatomical elements such as blood flow. Here, the otherwise strict requirement that the curve must pass through all data points may be relaxed. For example, the curve may be permitted to miss one or more data points except for the first and last data point, which according to some exemplary embodiments of the present invention must still be passed through by the curve. To measure how well the curve fits to the data points, error distances may be measured. The error distance may be defined as the distance between a data point and its "corresponding" point on the curve. The corresponding point on the curve may be a nearest point of the curve to the data point or the point of the curve that would have passed through the data point has the curve been required to pass through. The sum of all error distances may be added together and this sum may be minimized to follow the data points as nearly as is possible given the other constraints that affect curve shape.

Where confidence values and/or probability distributions are available for the measured points, they may be used with the approximation method 204 described above to define a cost function and constrain the curve approximation. For example, minimization of error distances may be combined with the confidence cost function. As the measure of confidence may be associated with each projection signal rather than being directly associated with a data point, a given data point may have a low confidence for one direction (e.g. x-axis coordinate) while having a high confidence for another direction (e.g. y-axis and/or z-axis coordinates). Accordingly, while one approach may still be used (either interpolation or approximation), the confidence data might only be used to adjust the curve in one or more directions for a given point.

Regardless of whether interpolation 203 or approximation 204 approaches are used, the data pertaining to the physical configuration of the device (e.g. the device definition information and model) 205 may be provided for reconstruction. In this context, the physical dimensions of the device, for example, information such as that described above and illustrated in FIG. 3, may be used to constrain the curve function. Elasticity and/or maximum allowable bending may also be among the device definition information and model 205. These values may either be calculated based on device design or may be empirically determined. For example, in designing a catheter for use in accordance with exemplary embodiments of the present invention, the pertinent device information may be procured.

The device information 205 may also be used in 3D model generation 209 and rendering 210, by making use of the knowledge of the positions and lengths of various elements of the device to determine the size and/or shape of the device at each distance therealong. This information may be expressed as a device section function/curve 207 as it may represent the approximate shape and/or size of the device at each section. The section function/curve may then be used during 3D model generation 209 and/or screen rendering 210 to modify the appearance of the displayed device model so that each element (for example, the electrodes) may be easily identifiable to the practitioner viewing the display and performing the intervention.

The curve function resulting from the reconstruction (203 or 204) may include a trajectory curve representing the fitting (interpolation or approximate) to the data points. Where the curve is determined not to be realistic (e.g., it is a degenerative curve) (Yes, 206), an appropriate warning may be displayed on screen 208. Where, however, the curve is considered to be realistic (e.g., not degenerative) (No, S206), for the purposes of providing a more intuitive display, a 3D model may be generated from the curve 209.

Figure 5:
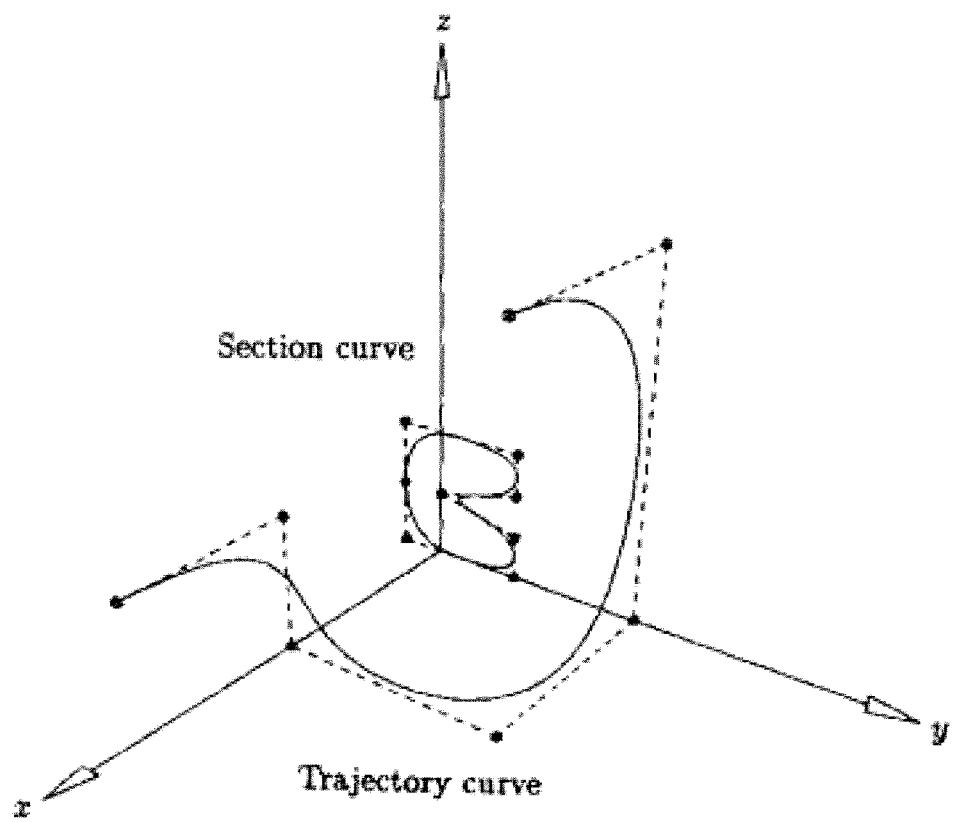
FIG. 5 is an illustration of a section curve and trajectory curve in accordance with exemplary embodiments of the present invention.
Figure 6:
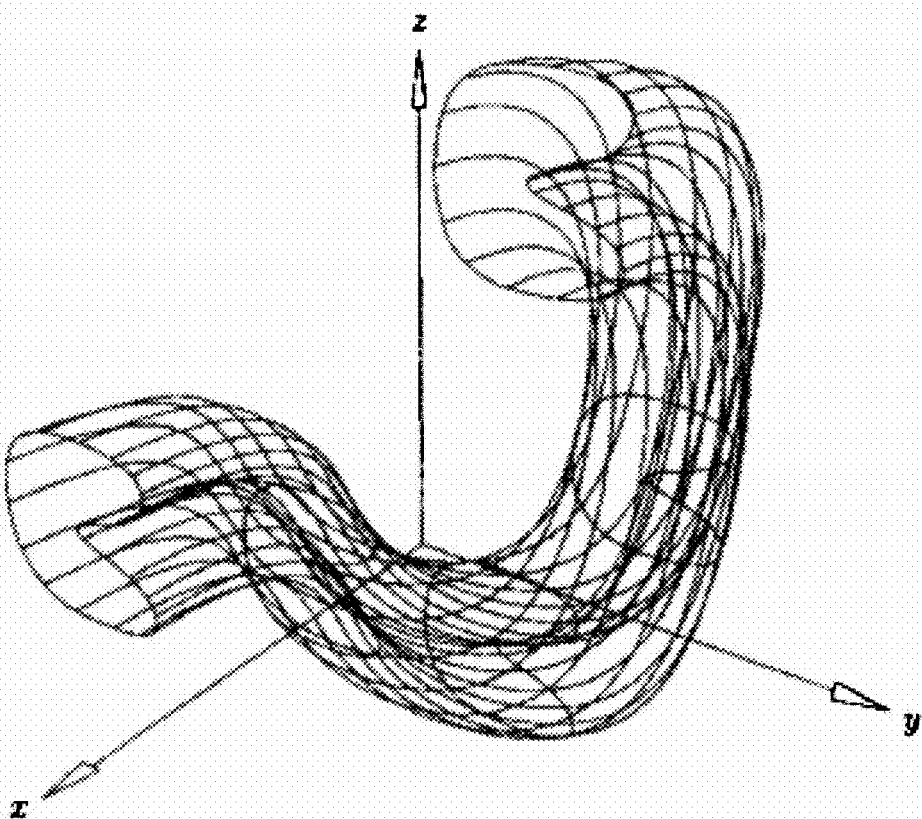
FIG. 6 is an illustration of a 3D device mesh produced by sweeping the section curve along the trajectory curve in accordance with exemplary embodiments of the present invention.

The 3D model may be a device mesh and may be produced by sweeping the section function/curve along the trajectory curve. To better illustrate this technique, FIG. 5 is an illustration of a section curve and trajectory curve in accordance with exemplary embodiments of the present invention and FIG. 6 is an illustration of a 3D device mesh produced by sweeping the section curve along the trajectory curve in accordance with exemplary embodiments of the present invention.

According to one approach, the section curve may be a circle with a radius that is dependent upon a thickness of the actual device with respect to distance. Alternatively the section curve may change shape and size with respect to distance thereby defining a more realistic representation of the device upon sweeping.

For example, the section curve may be scaled according to the device definition in order to emboss or carve elements of interest built-in on the device (e.g., coils, electrodes, etc.). Various elements may additionally be rendered in different colors to ease visual interpretation. Additionally, a half-sphere may be added at the device end to represent a device tip.

The model so generated may then be rendered for viewing 210, for example, using a GPU, from the full 3D model created in 209. The GPU rendering may then be displayed on a display device 211 to provide visual guidance to the practitioner performing the intervention.

Figure 7:
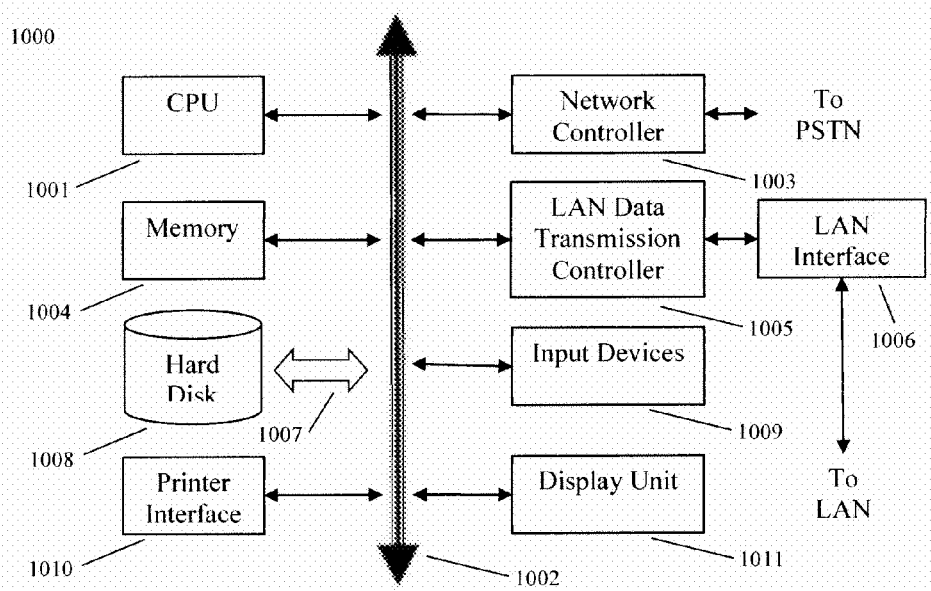
FIG. 7 shows an example of a computer system capable of implementing the method and apparatus according to embodiments of the present disclosure.

FIG. 7 shows an example of a computer system which may implement a method and system of the present disclosure. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

The computer system referred to generally as system 1000 may include, for example, a central processing unit (CPU) 1001, random access memory (RAM) 1004, a printer interface 1010, a display unit 1011, a local area network (LAN) data transmission controller 1005, a LAN interface 1006, a network controller 1003, an internal bus 1002, and one or more input devices 1009, for example, a keyboard, mouse etc. As shown, the system 1000 may be connected to a data storage device, for example, a hard disk, 1008 via a link 1007.

Exemplary embodiments described herein are illustrative, and many variations can be introduced without departing from the spirit of the disclosure or from the scope of the appended claims. For example, elements and/or features of different exemplary embodiments may be combined with each other and/or substituted for each other within the scope of this disclosure and appended claims.

What is claimed is:

1. A method for device visualization, comprising:
receiving a set of physical characteristics including a description of spatial relationships of a plurality of markers within a device;
acquiring radiographic data of the device within a subject;
identifying an approximate location of each of the plurality of markers within the radiographic data;
constructing a trajectory function for the device within the subject based on the identified approximate locations of each of the markers and the received set of physical characteristics;
constructing a 2D section function for the device based on the set of physical characteristics, wherein the 2D section function is substantially circular with a radius that is variably dependent upon a known thickness of the device over the trajectory function;
calculating a plurality of cross-sectional slices by calculating a shape of the 2D section function at intervals over the trajectory function;
generating a 3D model for the device by combining each of the plurality of calculated cross-sectional slices; and
displaying a rendering of the 3D model on a display device.

2. The method of claim 1 herein the device is a catheter and the plurality of markers include one or more micro-coils.

3. The method of claim 2, wherein the set of physical characteristics includes distances between adjacent micro-coils of the one or more micro-coils and a measure of maximum possible curvature or bending of the catheter.

4. The method of claim 1, wherein the trajectory function is a mathematical spline function defined by a knot vector, a vector of control points, and a degree of polynomial for the spline function.

5. The method of claim 4, wherein the knot vector and the vector of control points are varied to find a spline function which satisfies one or more constraints of the received set of physical characteristics.

6. The method of claim 5, wherein the spline function is a piecewise-polynomial function of a given degree of polynomial.

7. The method of claim 6, wherein the degree of polynomial for the spline function is three.

8. The method of claim 4, wherein a curve energy of the spline function is minimized.

9. The method of claim 4, wherein the spline function is a B-spline function.

10. The method of claim 4, wherein the spline function is a non-uniform rational B-spline (NURBS) function.

11. The method of claim 1, wherein the radiographic data is an MR image.

12. The method of claim 1, wherein the section function is a predetermined shape.

13. The method of claim 12, wherein the predetermined shape is a circle.

14. The method of claim 13, wherein the radius of the circle is dependent upon a length along the trajectory function.

15. The method of claim 1, wherein the 3D model is a 3D mesh and generating the 3D mesh.

16. The method of claim 1, wherein constructing the trajectory function includes interpolating a curve of the trajectory function through each of the identified approximate locations of the markers in a particular order.

17. The method of claim 1, wherein constructing the trajectory function includes approximating a curve of the trajectory function by permitting the curve to not intersect each identified approximate locations of the markers and by minimizing a sum of errors calculated as a distance between each identified approximate location of the markers and a corresponding point along the curve.

18. The method of claim 17, wherein identifying an approximate location of each of the plurality of markers within the radiographic data includes determining a confidence or probability for the approximate locations.

19. The method of claim 1, wherein prior to generating the 3D model, it is determined whether the trajectory function is degenerative and where the trajectory function is determined to be degenerative, a warning message is displayed on the display device.

20. A method for providing visualization for intervention guidance, comprising:
    acquiring a radiographic study;
    identifying a set of markers within a device within the acquired radiographic study;
    fitting a curve to the identified set of markers according to locations of the identified set of markers within the radiographic study and a prior knowledge of physical characteristics of the device;
    calculating a plurality of cross-sectional slices by calculating a shape of a deformable model of the device at intervals over the fitted curve;
    generating a 3D model for the device by combining each of the plurality of calculated cross-sectional slices; and
    displaying a rendering of the 3D model on a display device for intervention guidance,
    wherein the a prior knowledge of physical characteristics of the device includes distances between markers within the device and a maximum possible degree of curvature or bending of the device.

21. The method of claim 20, wherein the curve is a mathematical spline function defined by a knot vector, a vector of control points, and a degree of polynomial for the spline function and the knot vector and the vector of control points are varied to find a spline function which satisfies one or more constraints of the a prior knowledge of the physical characteristics of the device.

22. A computer system comprising:
    a processor; and
    a non-transitory, tangible, program storage medium, readable by the computer system, embodying a program of instructions executable by the processor to perform method steps for device visualization, the method comprising:
    receiving a set of physical characteristics including a description of spatial relationships of a plurality of markers within a device;
    acquiring a radiographic scan of the device within a subject;
    identifying an approximate location of each of the plurality of markers within the radiographic scan;
    constructing a mathematical spline function for the device within the subject based on the identified approximate locations of each of the markers and the received set of physical characteristics;
    constructing a 2D section function for the device based on the received set of physical characteristics, wherein the 2D section function is substantially circular with a radius that is variably dependent upon a known thickness of the device over the trajectory function;
    calculating a plurality of cross-sectional slices by calculating a shape of the 2D section function at intervals over the trajectory function;
    generating a 3D model for the device by combining each of the plurality of calculated cross-sectional slices; and
    displaying a rendering of the 3D model on a display device.

* * * * *